(12) United States Patent
Stoddard et al.

(10) Patent No.: US 7,033,353 B2
(45) Date of Patent: *Apr. 25, 2006

(54) ELECTROSURGICAL GAS ATTACHMENT

(75) Inventors: Robert Bryant Stoddard, Louisville, CO (US); Cliff Rodes Ketcham, Boulder, CO (US); Arlan James Reschke, Longmont, CO (US)

(73) Assignee: Sherwood Services AG, Schaffhausen (CH)

( * ) Notice: Subject to any disclaimer, the term of this patent is extended or adjusted under 35 U.S.C. 154(b) by 259 days.

This patent is subject to a terminal disclaimer.

(21) Appl. No.: 10/628,682

(22) Filed: Jul. 28, 2003

(65) Prior Publication Data

US 2004/0167512 A1    Aug. 26, 2004

Related U.S. Application Data

(63) Continuation of application No. 09/712,538, filed on Nov. 14, 2000, now Pat. No. 6,602,249, which is a continuation of application No. 08/621,151, filed on Mar. 21, 1996, now abandoned.

(51) Int. Cl.
*A61B 18/18* (2006.01)

(52) U.S. Cl. .................................................. 606/41
(58) Field of Classification Search ............ 606/41, 606/45, 47, 34
See application file for complete search history.

(56) References Cited

U.S. PATENT DOCUMENTS

| | | | |
|---|---|---|---|
| 3,595,239 A | 7/1971 | Petersen | |
| 3,838,242 A | 9/1974 | Goucher | |
| 4,209,018 A | 6/1980 | Meinke et al. | |
| 4,781,175 A | 11/1988 | McGreevy et al. | |
| 5,041,110 A | 8/1991 | Fleenor | |
| 5,088,997 A | 2/1992 | Delahuerga et al. | |
| 5,108,389 A | 4/1992 | Cosmescu | |
| 5,152,762 A | 10/1992 | McElhenney | |
| 5,160,334 A | 11/1992 | Billings et al. | |
| 5,217,457 A | 6/1993 | Delahuerga et al. | |
| 5,244,462 A | 9/1993 | Delahuerga et al. | |
| 5,324,283 A | 6/1994 | Heckele | |
| 6,602,249 B1 * | 8/2003 | Stoddard et al. .............. | 606/45 |

* cited by examiner

*Primary Examiner*—David M. Shay

(57) ABSTRACT

A nozzle and electrode combination for use with an electrosurgical device is described. The nozzle includes a shroud defining a channel and a lumen which intersect to define an acute angle. An electrode is positioned within the channel and includes a distal end extending from a distal portion of the shroud and a proximal end extending from the proximal portion of the shroud. An end cap positioned adjacent the proximal portion of the shroud about the electrode is preferably overmolded to the shroud and the electrode. Preferably, a portion of the walls defining the channel and/or the lumen include conductive material which communicates with the electrode to eliminate electric potential within the shroud.

14 Claims, 4 Drawing Sheets

ELECTROSURGICAL GAS ATTACHMENT

RELATED APPLICATIONS

This application is a Continuation of U.S. patent application Ser. No. 09/712,538 filed on Nov. 14, 2000, now U.S. Pat. No. 6,602,249, which is a Continuation of U.S. patent application Ser. No. 08/621,151 filed on Mar. 21, 1996, now abandoned, the entire contents each are incorporated herein by reference.

BACKGROUND OF THE INVENTION

This invention relates to a nozzle and electrode combination and method of manufacturing a gas seal therebetween and specifically the injection and over molding of a shroud and end cap to the electrode.

BACKGROUND OF THE DISCLOSURE

U.S. Pat. No. 3,595,239 has a catheter with a removable axial electrode and a proximal side port to receive fluid to inflate the catheter tube. Inert gas, such as argon, delivered concurrently with electrosurgical energy forms an ionized path for energy flow from an electrode in the distal end of the electrosurgical pencil. Commercially available gas electrosurgical pencils are made specially for controlled delivery of argon and electrosurgical energy delivery. Gas surgical pencils have a pair of switches that start and stop argon flow as disclosed in U.S. Pat. Nos. 5,217,457; 5,244,462 and 5,088,997 all assigned to the same assignee as this disclosure. The switch for directing argon flow mounts on the electrosurgical pencil. A gas line for argon and a pair of switches for the electrosurgical generator coagulation or cut wave forms are on the pencil. The argon electrosurgical pencil includes an electrical cable with wires for connection directly to the gas surgical unit to trigger the flow of argon gas when the electrosurgical energy is called for by the surgeon. The gas delivery control is on the pencil and controls the gas delivery from the separate on and off switch buttons and wires connecting to circuits integral with the gas surgical unit. In addition to the three wires connected between the argon electrosurgical pencil and the gas surgical unit, there is another wire for providing electrosurgical energy from the electrosurgical generator. Cut and coagulation wave forms are controlled by buttons therefor on the gas surgical pencil.

A standard electrosurgical pencil without argon gas plumbing or an extra wire is made in high volume and cost about half of that for an argon electrosurgical pencil. Adapting a standard pencil to operate the gas surgical unit offers lower cost to practitioners that have never used argon with electrosurgery and to those who infrequently use argon electrosurgery due to added cost.

U.S. Pat. No. 4,781,175 has an argon electrosurgical pencil with a sensing lumen to determine the proper operation of the pencil by return of gas to the delivery apparatus thus verifying a proper connection and flow of the gas at the nozzle. Thus, the gas delivery apparatus responds accordingly.

U.S. Pat. No. 5,324,283 has a switch on an endoscope. The switch breaks a light path through optic fibers to control external accessories remotely turned on and off. U.S. Pat. No. 4,209,018 has a tissue coagulation apparatus with indicating means in circuit with the active and return electrode leads. An output signal from the indicating means provides information to a control for the electrosurgical generator. The specific indicating means can respond to various physical values showing the presence and strength of an electrical arc between the distal ends of bipolar electrodes. The device controls the strength of the arc so heat applied during electrosurgery is minimized to avoid tissue cell rupture and/or burning of albumin. The monitoring function provided by the indicating means controls internal circuitry within the electrosurgical generator by means of wiring directly to the generator. There is no teaching of the indicating means controlling something external of the generator such as the argon delivery from a gas surgical unit. The electrically connected (hard wired) indicating means is merely external pickup for the control and does not have an external output for another device such as a gas surgical unit.

Any number of internal inductive pickups has been proposed and used for control of RF leakage. U.S. Pat. No. 5,152,762 discloses an inductive pickup and references prior patents that use a winding on a common magnetic core about which the active and return leads are also wound. When there is an unbalanced between the flow of current through the active and return leads an EMF is generated in the extra winding. That EMF is used as a signal to control the RF leakage and maintain balanced flow of energy in the active and return leads. Inductive coils for leakage are internal with respect to the electrosurgical generator and as such precede the output connections on the exterior of the generator. They are sensitive to inductive differences in the active and return leads, but provide no external signal for use with an accessory.

U.S. Pat. No. 5,160,334 has an electrosurgical generator and suction apparatus with a switching circuit connected to a hand switch or foot switch to operate the electrosurgical generator remotely. The switching circuit activates a controller for a vacuum motor plumbed to remove the smoke that results at the site of the electrosurgery. Clearly the remote operation of the switching circuit for the smoke evacuator by the hand or foot switch is hard wired, i.e., passes through internal wires in the electrosurgical unit. This approach as well as those described are disadvantageous to the many of existing electrosurgical generators presently in operation in hospitals throughout the world. The internal wiring for automatic activation of the suction or the like accessory is required in the electrosurgical generator. It is desired to be able to have an automatic activation that easily starts and stops the argon gas flow and is external to the electrosurgical generator, gas surgical unit and the standard of electrosurgical pencil.

U.S. Pat. No. 5,108,389 discloses an automatic activation circuit for a smoke evacuator used with a laser. A foot switch breaks a laser beam and signals for operating the smoke evacuator. There is no physical association or direct electrical coupling or attachment between the laser and the smoke evacuator. That is to say that, when the laser beam is transmitted and received and the foot switch interrupts the laser beam the control signal comes from the foot switch not the laser.

U.S. Pat. No. 5,041,110 discloses a cart for supporting an electrosurgical generator, gas supply with automatic valves and a control logic panel. This cart adapts the many different existing electrosurgical generators for use with argon gas. While the term, "electrosurgical pencil" is repeatedly referred to throughout the '110 patent, the disclosure therein is made only to a special gas electrosurgical pencil. In particular, a gas tube connects to the pencil to supply the inert argon through a passage in the pencil hand piece and about a wire carrying the electrosurgical energy. There is no switch control on the pencil and no suggestion of how a standard pencil could be used. Moreover, the activation of the combined gas tube and special electrosurgical pencil is merely by a foot switch. The control logic panel is electrically connected to the gas flow control valve assembly and the electrosurgical generator for the control of gas flow and electrosurgical energy from the foot switch.

There remains a need to be able to adapt the inexpensive standard electrosurgical pencil for activation of the argon flow from a gas surgical unit. Readily available, inexpensive and high volume electrosurgical pencil thus can be used to start and stop the flow of argon during electrosurgery. The circuit disclosed responds to the surgeon's request for electrosurgery made at the electrosurgical pencil cut or coagulation buttons. The circuit concurrently delivers argon to a special gas electrode fit to the distal end of a standard electrosurgical pencil. The special gas electrode is the subject of U.S. application Ser. No. 08/619,380 titled "Circuit And Method For Argon Activation", filed Mar. 21, 1996 and is assigned to the same assignee. The references noted herein are incorporated by reference and made a part of this disclosure.

SUMMARY OF THE INVENTION

A circuit for concurrent activation of a gas surgical unit flow control valve and an electrosurgical generator upon the surgeon's operation of an electrosurgical energy request button on an electrosurgical pencil is disclosed. The circuit preferably has an automatic switch connected to receive current flow when the energy request button is operated by the surgeon. The automatic switch opens or closes when the energy request button is opened or closed respectively by the surgeon. The automatic switch connects to the gas surgical unit flow control valve and operates it to send inert gas to the electrosurgical pencil. The automatic switch connects to the electrosurgical generator, operates it and delivers selectively electrosurgical energy to the electrosurgical pencil.

The circuit responds if the surgeon uses the electrosurgical energy request button on the electrosurgical pencil to obtain a cut wave form or a coagulation wave form from the electrosurgical generator.

An electrode and nozzle combination preferably transports ionizable gas to a tip on an electrosurgical instrument for gas enhanced electrosurgery by a surgeon on a patient. An electrode in the preferred embodiment has a proximal end, a distal end, and a length therebetween. The length may be substantially along an axis A. A shroud most preferably surrounds the electrode along its length leaving the proximal and distal ends of the electrode exposed. A patient part on the shroud preferably points toward or faces the patient. A rear part on the shroud preferably points toward the rear or the pencil that the surgeon would hold. The patient and rear parts in the preferred embodiment align substantially along axis A. A passage between the patient part and the rear part might define a space within the shroud and about the length. At least one port in the shroud may contain a lumen protruding from the shroud toward the proximal end at an angle to the axis A. The lumen preferably connects with the passage for fluid communication therebetween.

An end cap in the preferred embodiment attaches to the proximal end for surrounding the electrode and for forming a gas tight seal between the proximal end and the rear part of the shroud. A complimentary portion on the rear part and an anti rotation lock on the end cap most preferably engage to prevent relative rotary motion therebetween. The anti rotation lock and the complimentary portion each have, in the preferred embodiment, hexagonal conjugating features thereon. An anti twist posterior on the end cap is preferably shaped to interengage with the electrosurgical pencil to prevent relative rotation therebetween. The anti twist posterior and the electrosurgical pencil each may have hexagonal interengaging features thereon.

The shroud and end cap are in the preferred structure polymers that can be injection and overmolded, respectively about and then to the electrode for forming a gas tight seal of the rear part of the passage and at the proximal end. The angle between the lumen and the axis A might be acute so the port is approximately adjacent the end cap. The shroud may be injection molded and the end cap could be overmolded to the shroud and the electrode proximal end. The passage might then be substantially along axis A and coaxial with respect to the length. A recess on the rear part could receive thereover and therewithin a projection on the end cap formed during molding.

A method of manufacturing a gas tight seal between a shroud and an electrode may be by injection molding the shroud. The shroud may be made with the passage therethrough, the patient part pointed toward the patient and the rear part pointed aft. The shroud is preferably injection molded with at least one port containing the lumen protruding therefrom toward the proximal end at an acute angle to the passage so the lumen and the passage may connect for fluid communication. Fixturing the electrode within the passage without contact between the shroud and the electrode is a preferred step of the method. Another step that is preferred may include overmolding the end cap to the shroud for attaching the electrode and to form the gas tight seal with the proximal end near the rear part of the shroud.

The method of manufacturing the gas tight seal between the shroud and the electrode might have the step of fixturing the electrode substantial coaxial within the passage and with the electrode tip extending from the patient part. The method of manufacturing could include the step of overmolding the electrode for forming the end cap between the shroud and the electrode at the rear part while the electrode is fixtured.

DETAILED DESCRIPTION OF THE INVENTION

Figure 1:
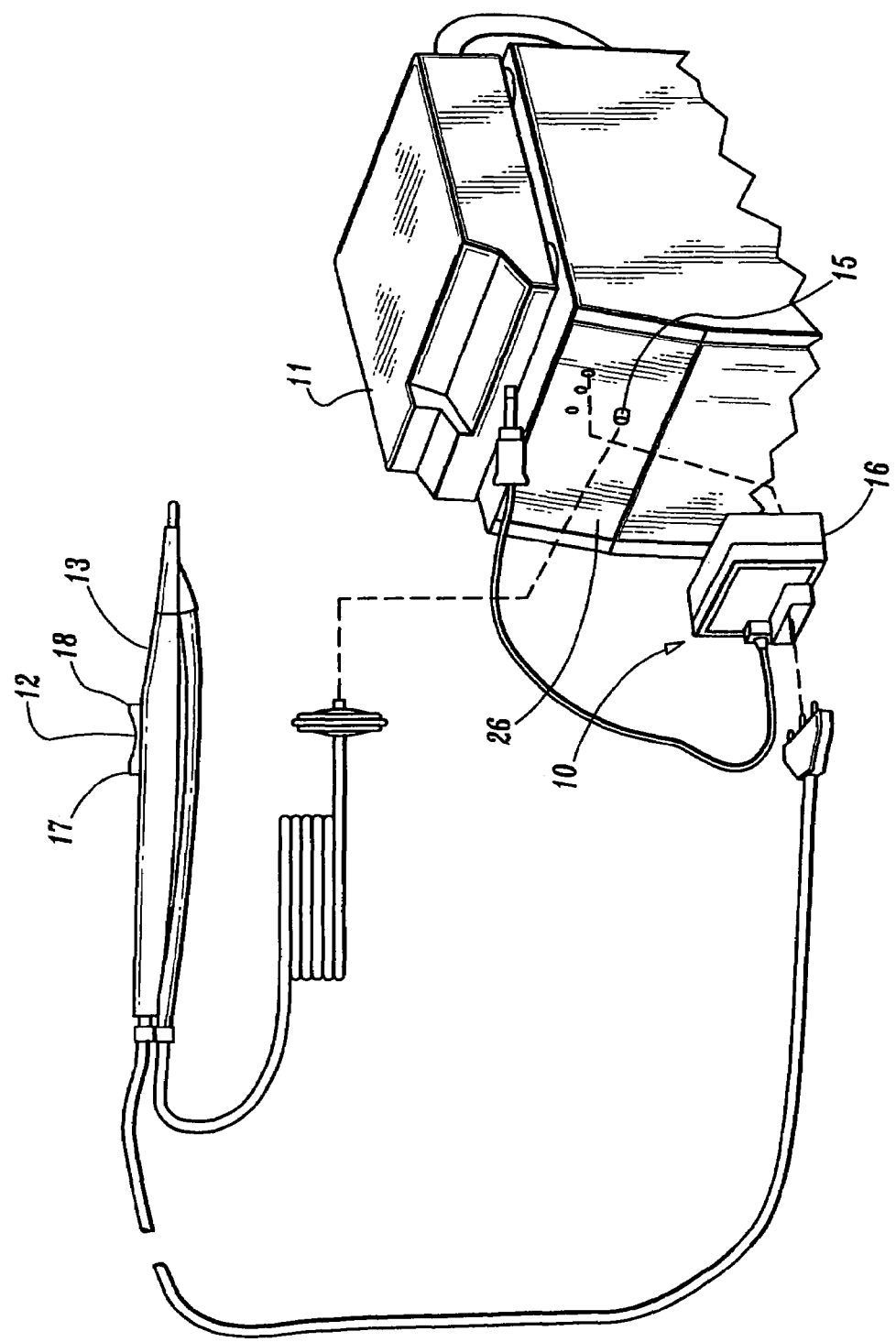
FIG. 1 is a schematic perspective view of a system having a gas surgical unit flow control valve and an electrosurgical generator concurrently activated upon the surgeon's operation of an electrosurgical energy request button on an electrosurgical pencil.

A circuit 10 for the system for concurrent activation of a gas surgical unit flow control valve and an electrosurgical generator 11 upon the surgeon's operation of an electrosurgical energy request button 12 on an electrosurgical pencil 13 is disclosed in FIG. 1. The circuit 10 has an electrosurgical pencil 13 such as E2502B, E2515, E2516, E2525, E2550 manufactured by Valleylab of Boulder, Colo. and for supplying power in the circuit 10 a nine volt battery activates an automatic switch to provide simultaneous flow of electrosurgical energy from the electrosurgical generator 11 and flow of inert gas from the gas surgical unit flow control valve 15 in FIG. 1. An automatic switch 16 receives the flow of current upon the operation of the energy request button 12 by the surgeon. The automatic switch 16 opens or closes when the energy request button 12 is opened or closed, respectively by the surgeon. The automatic switch 16, which is connected to the gas surgical unit flow control valve 15, operates control valve 15 to send inert gas to the electrosurgical pencil 13. The automatic switch 16 is connected to the electrosurgical generator 11 and operates to selectively deliver electrosurgical energy to the electrosurgical pencil 13.

The circuit 10 responds if the surgeon uses the electrosurgical energy request button 12 on the electrosurgical pencil 13 to obtain a cut wave form or a coagulation wave form from the electrosurgical generator 11. Standard electrosurgical pencils such as those mentioned herein include two separate switch buttons 17 and 18, one for cutting and another for coagulating.

The gas surgical unit flow control valve 15 of FIG. 1 has tubing shown connected to the electrosurgical pencil 13. The delivery of an ionizable gas such as argon is the subject of this disclosure and in particular, the manifolding of the gas to the electrode of the electrosurgical pencil 13 during enhanced electrosurgery. Automatic switch 16 is located between electrosurgical pencil 13 and the gas surgical unit 26. The preferred gas surgical unit is made by Valleylab of Boulder, Colo. as the GSU or Force Argon unit. The three connections shown in FIG. 1 activate the gas control valve 15 for cut or coagulation. With regard to the latter, the connections pass through the gas surgical unit 26 and connect via a foot switch terminal (not shown) to the electrosurgical generator 11. In FIG. 1 the gas control valve 15 is shown schematically. Skilled artisans will understand that such valves are electrically activated, for example by solenoid, to start and stop gas flow. A convenient form of the circuit 10 is thus shown as a box in FIG. 1. In that box the components of circuit 10 are provided.

Figure 2:
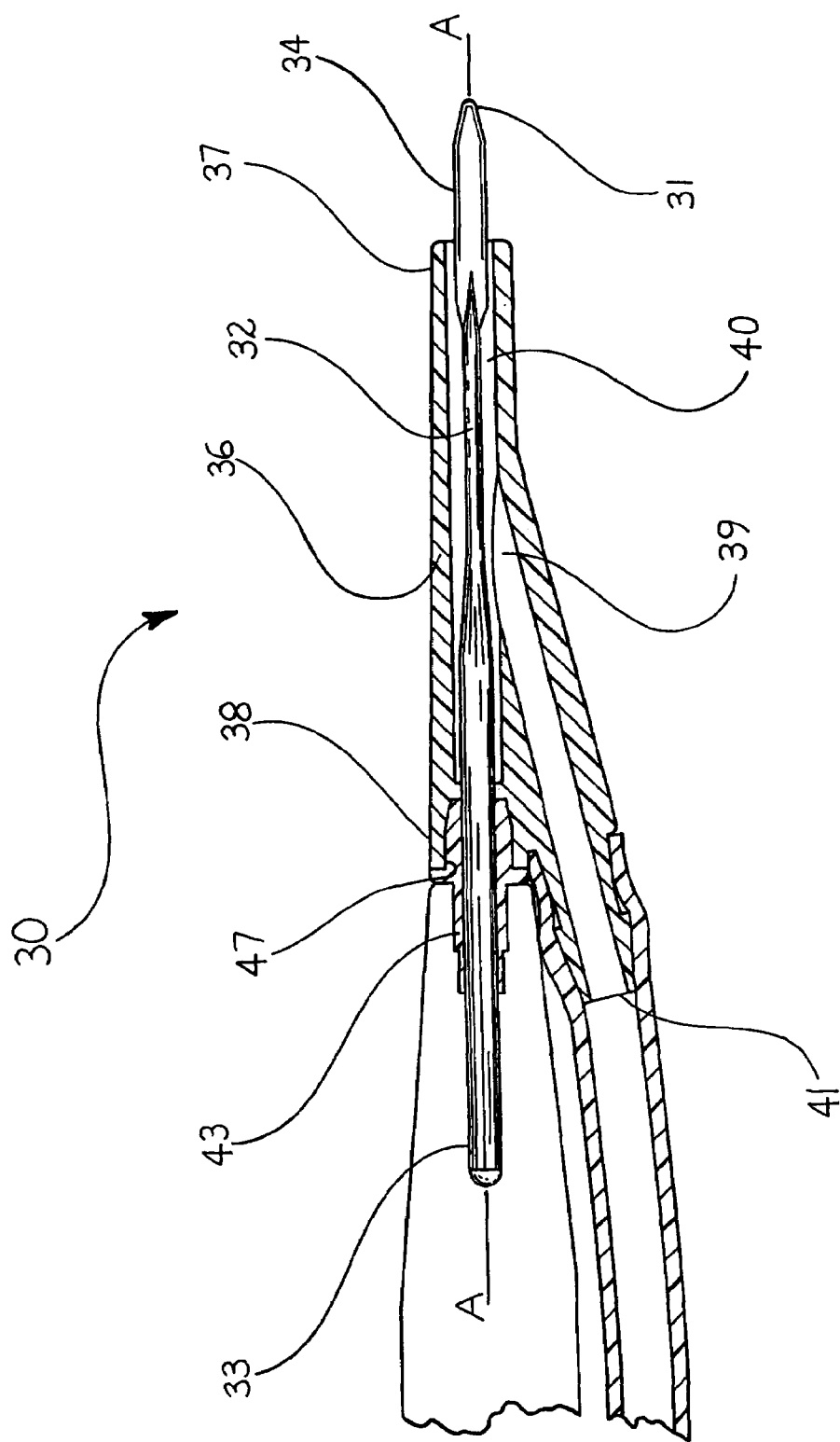
FIG. 2 is a side view in cross section taken along line 2—2 of FIG. 1 for showing the relative coaxial relationship of the electrode and the shroud in the nozzle and electrode combination.
Figure 3:
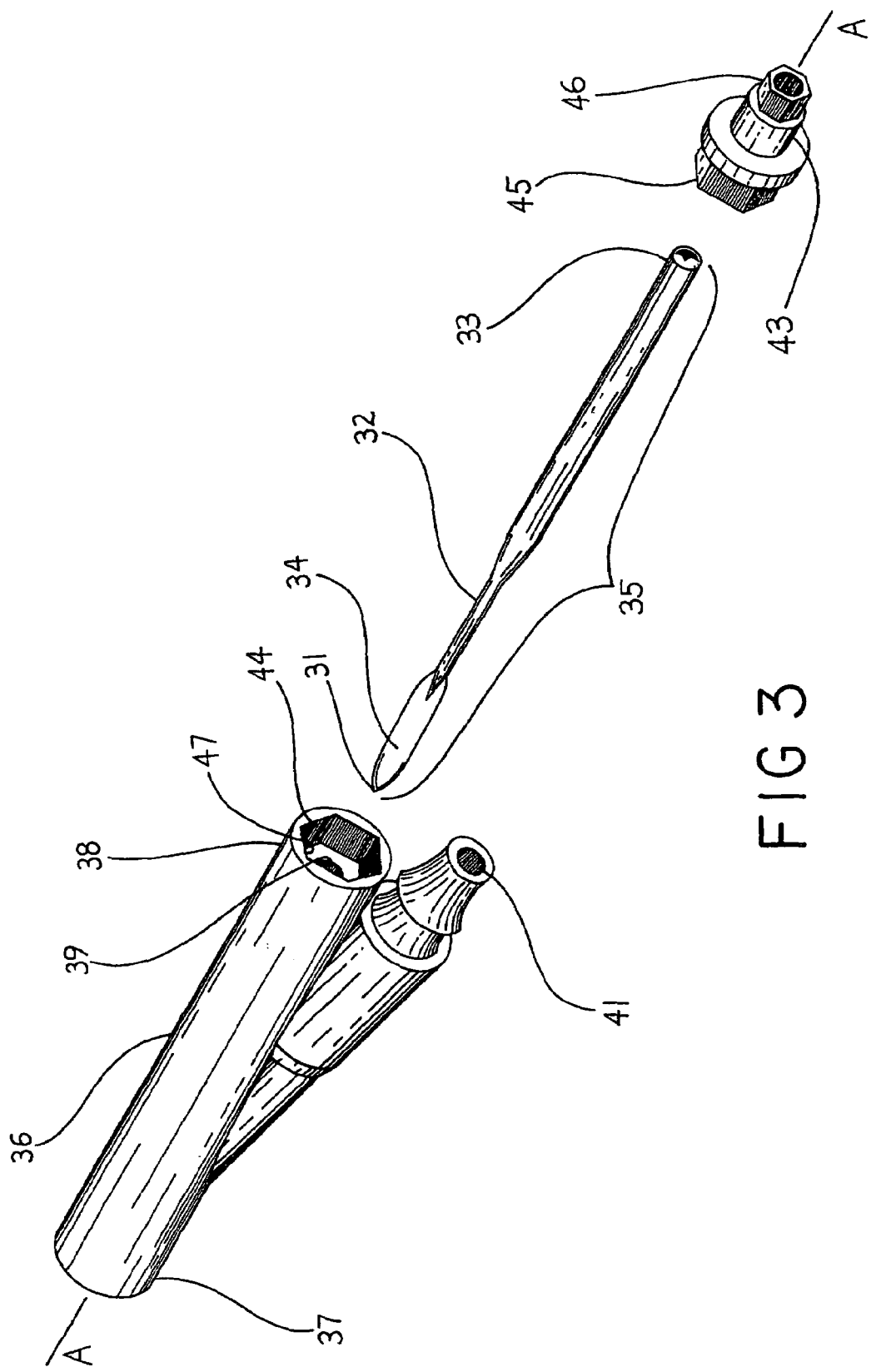
FIG. 3 is an exploded view of the shroud, electrode and end cap as would be seen from the pencil end of the nozzle and electrode combination.
Figure 4:
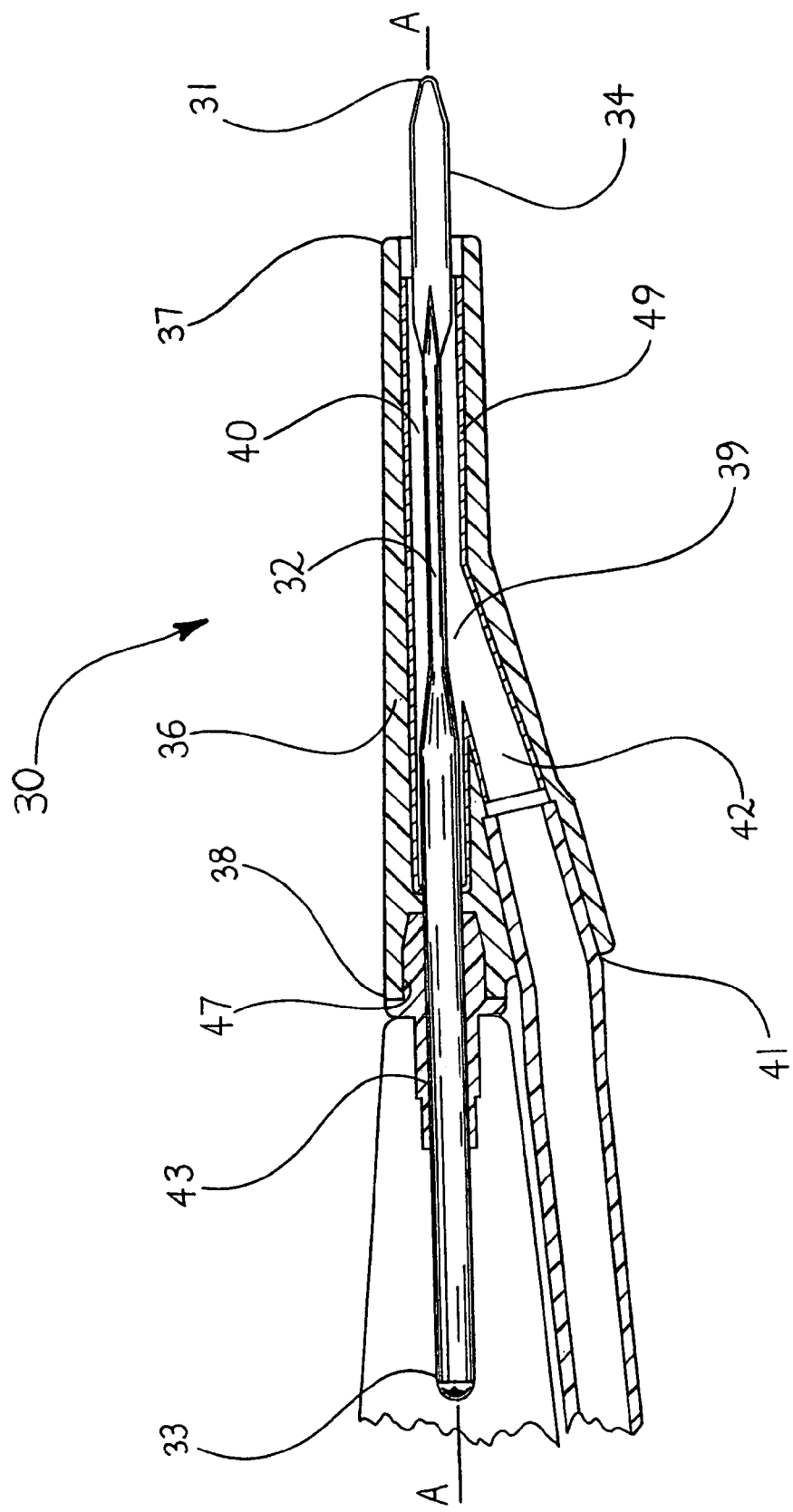
FIG. 4 is a side view in cross section taken along line 2—2 of FIG. 1 for showing an alternate shroud in the nozzle the relative coaxial relationship of the electrode and the shroud in the nozzle and electrode combination.

An electrode and nozzle combination 30 for transporting ionizable gas to a tip 31 on an electrosurgical instrument for gas enhanced electrosurgery by a surgeon on a patient is shown in FIGS. 1, 2, 3 and 4. An electrode 32 has a proximal end 33, a distal end 34, and an intermediate portion having a length 35 therebetween that is substantially along an axis A as best shown in the side view of FIGS. 2 and 4 and the exploded view of FIG. 3. A shroud 36 surrounds the intermediate portion of electrode 32 along its length 35 and leaves the proximal and distal ends 33 and 34 of the electrode exposed. A patient part or distal portion 37 of the shroud 36 points toward or faces the patient (not shown). A rear part or proximal portion 38 of the shroud 36 points toward the rear of the pencil that the surgeon would hold. The distal and proximal portions 37 and 38 of shroud 36 are substantially aligned along axis A. A passage or channel 39 between the distal portion 37 and proximal portion 38 defines a space 40 within the shroud 36 which is about equal in length to the length 35 as best depicted in FIG. 2. At least one port 41 in the shroud 36 defines a lumen 42 which extends from the shroud 36 toward the proximal end 33 of electrode 32 at an angle to the axis A in FIG. 4. The lumen 42 connects with the passage 39 for fluid communication therebetween as seen in FIGS. 2 and 4. In an alternate embodiment shown in FIG. 4, a conductive coating 49 is formed on the inside wall of shroud 36 and port 41 and connects electrically near the end cap 43 to the electrode 32 for eliminating the electrical potential in the gas carrying space 39 and 40 therewithin. Nozzle 30 shown in FIG. 2 has another way of insulating to protect the surgeon. Specifically, the port 41 includes a connector 41a and a high dielectric tube, preferably formed of silicone.

An end cap 43 is attached to the proximal end 33 of the electrode 32 and forms a gas tight seal between the proximal end 33 and the proximal portion 38 of the shroud 36. A complimentary portion 44 is provided on the proximal portion 38 of shroud 36 and an anti rotation lock 45, i.e., hex head, is provided on the end cap 43 for engaging the complimentary portion 44 to prevent relative rotary motion therebetween as best illustrated in the exploded view of FIG. 3. The anti rotation lock 45 and the complimentary portion 44 each have hexagonal conjugating features thereon. An anti twist posterior 46 on the end cap 43 shaped to interengage with the electrosurgical pencil 13 prevents relative rotation therebetween. The anti twist posterior 46 and the electrosurgical pencil 13 also have hexagonal interengaging features thereon in the preferred embodiment.

The shroud 36 and end cap 43 are formed of polymers that can be injection and overmolded, respectively to the electrode 32 for forming a gas tight seal for the passage 39 about the proximal end 33 of electrode 32 and with the proximal portion 38. The angle between the longitudinal axis of the lumen 42 and the axis A is acute and is preferably about 12.6 degrees but may be in the range of 10 to 20 degrees. The proximal end of port 41 is positioned approximately adjacent the end cap 43 as seen in FIGS. 2 and 3. The shroud 36 is injection molded and the end cap 43 is overmolded to the shroud 36 and the electrode 32 at proximal end 33. A recess 47 in FIG. 3 on the proximal portion 38 of shroud 36 receives thereover and therewithin a projection on the end cap 43 formed during molding as seen in cross section in FIG. 2.

A method of manufacturing a gas tight seal between shroud 36 and electrode 32 includes injection molding the shroud 36. The shroud 36 is injection molded with passage 39 therethrough, the distal end 37 pointed toward the patient and proximal portion 38 pointed aft. The shroud 36 is injection molded with at least one port 41 containing lumen 42 protruding therefrom toward the proximal end 38 at an acute angle to the passage 39 so the lumen 42 and the passage 39 connect for fluid communication. Fixturing the electrode 32 within the passage 39 without contact between the shroud 36 and the electrode 32 is a step of the method. Another step is overmolding end cap 43 to the shroud 36 for attaching the electrode 32 and to form the gas tight seal in the rear part 38 of the shroud 36.

The method of manufacturing the gas tight seal between the shroud 36 and the electrode 32 has the step of fixturing the electrode 32 substantial coaxial within the passage 39 and with the electrode tip 31 extending from the distal portion 37 of shroud 36. The method of manufacturing includes the step of overmolding the electrode 32 for forming the end cap 43 between the shroud 36 and the electrode 32 at the proximal portion 38 while the electrode 32 is fixtured.

An electrode and nozzle combination 30 and method of manufacture thereof have been disclosed with specificity. Skilled artisans could substitute other components and method steps and achieve similar benefits and advantages. The claims that follow seek to cover all such possibilities.

What is claimed is:

1. An electrode and nozzle assembly for use with an electrosurgical device comprising:
 a shroud including a distal portion and a proximal portion, the shroud defining a channel having a longitudinal axis and extending between the distal portion and the proximal portion, the channel being open at each end;
 a conductive coating positioned on an internal wall of at least a portion of the channel; and
 an electrode positioned within the channel, the electrode having a distal end extending from the distal portion of the shroud and a proximal end extending from the proximal portion of the shroud.

2. An electrode and nozzle assembly as recited in claim 1, wherein a proximal end of the channel has a smaller diameter than the distal end of the channel.

3. An electrode and nozzle assembly according to claim 1, wherein the shroud further comprises a port defining a lumen, the lumen communicating with the channel, a longitudinal axis of the lumen intersecting the longitudinal axis of the channel to define an acute angle.

4. An electrode and nozzle assembly as recited in claim 3, wherein the acute angle is between about 10 degrees and about 20 degrees.

5. An electrode and nozzle assembly as recited in claim 4, wherein the acute angle is about 12.6 degrees.

6. An electrode and nozzle assembly as recited in claim 1, further comprising an end cap positioned adjacent the proximal portion of the shroud about the electrode, the end cap being overmolded to the shroud and to the electrode.

7. An electrode and nozzle assembly as recited in claim 6, wherein a recess is formed in the proximal portion of the shroud, the end cap being positioned within the recess.

8. An electrode and nozzle assembly as recited in claim 7, wherein at least a portion of the recess and at least a portion of the end cap have a hexagonal configuration.

9. An electrode and nozzle assembly for use with an electrosurgical device comprising:
 a shroud including a distal portion and a proximal portion, a channel defining a longitudinal axis and extending between the distal portion and the proximal portion, the channel being open at each end, and a port defining a lumen, the lumen communicating with the channel, the longitudinal axis of the lumen intersecting the longitudinal axis of the channel to define an acute angle;
 a conductive coating positioned on an internal wall of at least a portion of the channel and the lumen;
 an electrode positioned within the channel, the electrode having a distal end extending from the distal portion of the shroud and a proximal end extending from the proximal portion of the shroud; and
 an end cap positioned adjacent the proximal portion of the shroud about the electrode, the end cap being overmolded to the shroud and to the electrode.

10. An electrode and nozzle assembly as recited in claim 9, wherein a proximal end of the channel has a smaller diameter than the distal end of the channel.

11. An electrode and nozzle assembly as recited in claim 9, wherein the acute angle is between about 10 degrees and about 20 degrees.

12. An electrode and nozzle assembly as recited in claim 11, wherein the acute angle is about 12.6 degrees.

13. An electrode and nozzle assembly as recited in claim 9, wherein a recess is formed in the proximal portion of the shroud, the end cap being positioned within the recess.

14. An electrode and nozzle assembly as recited in claim 13, wherein at least a portion of the recess and at least a portion of the end cap have a hexagonal configuration.

* * * * *